United States Patent
Mastenbroek et al.

(10) Patent No.: US 9,615,587 B2
(45) Date of Patent: Apr. 11, 2017

(54) METHOD TO PRODUCE CAKE

(75) Inventors: José Mastenbroek, The Hague (NL);
Jan Dirk Rene Hille, Wouw (NL);
Arjen Sein, Leiden (NL); Arie Gerrit Terdu, Strijen (NL)

(73) Assignee: DSM IP ASSETS B.V., Heerlen (NL)

( * ) Notice: Subject to any disclaimer, the term of this patent is extended or adjusted under 35 U.S.C. 154(b) by 517 days.

(21) Appl. No.: 12/524,749

(22) PCT Filed: Jan. 30, 2008

(86) PCT No.: PCT/EP2008/051147
§ 371 (c)(1),
(2), (4) Date: Nov. 5, 2009

(87) PCT Pub. No.: WO2008/092907
PCT Pub. Date: Aug. 7, 2008

(65) Prior Publication Data
US 2010/0062106 A1   Mar. 11, 2010

(30) Foreign Application Priority Data

Feb. 1, 2007 (EP) .................... 07101567
Jul. 19, 2007 (EP) .................... 07112741

(51) Int. Cl.
| | | |
|---|---|---|
| A21D 10/00 | (2006.01) | |
| A21D 2/02 | (2006.01) | |
| A21D 8/04 | (2006.01) | |
| A21D 10/04 | (2006.01) | |
| A21D 2/18 | (2006.01) | |
| A21D 2/26 | (2006.01) | |
| A21D 13/068 | (2017.01) | |
| A23L 15/00 | (2016.01) | |
| C12N 9/00 | (2006.01) | |

(52) U.S. Cl.
CPC .............. *A21D 2/02* (2013.01); *A21D 2/186* (2013.01); *A21D 2/26* (2013.01); *A21D 8/042* (2013.01); *A21D 8/047* (2013.01); *A21D 10/04* (2013.01); *A21D 13/068* (2013.01); *A23L 15/25* (2016.08); *C12Y 301/01004* (2013.01); *A23V 2002/00* (2013.01)

(58) Field of Classification Search
USPC ......................................... 426/20
See application file for complete search history.

(56) References Cited

U.S. PATENT DOCUMENTS

| | | | | |
|---|---|---|---|---|
| 4,567,046 | A * | 1/1986 | Inoue et al. .................. | 426/20 |
| 6,007,851 | A * | 12/1999 | Schoenmaker et al. ........ | 426/46 |
| 6,143,545 | A | 11/2000 | Clausen et al. | |
| 6,403,144 | B1 * | 6/2002 | El-Khoury et al. ........... | 426/662 |
| 2001/0055635 | A1 * | 12/2001 | Spendler et al. ............... | 426/20 |
| 2003/0124647 | A1 | 7/2003 | Sorensen et al. | |
| 2003/0175383 | A1 | 9/2003 | Bojsen et al. | |

FOREIGN PATENT DOCUMENTS

| | | |
|---|---|---|
| EP | 0 426 211 | 5/1991 |
| EP | 0 531 104 | 3/1993 |
| EP | 0993777 | 4/2000 |
| EP | 1 145 637 | 10/2001 |
| JP | 2005-268911 | 10/1993 |
| JP | 2001-204372 | 7/2000 |
| JP | 2003-325140 | 11/2003 |
| WO | WO 01/47363 | 7/2001 |
| WO | 2004/097012 A2 | 11/2004 |
| WO | WO 2005/099487 | 10/2005 |
| WO | WO 2008/025674 | 3/2008 |

OTHER PUBLICATIONS

Welcher, Low Fat Calorie Chiffon Cake, Food.com, Mar. 27, 2003, accessed at http://www.food.com/recipe/low-fat-low-calorie-chiffon-cake-57357.*
Carol, Chiffon Cake, Allrecipes.com, Jun. 25, 2003, http://allrecipes.com/recipe/chiffon-cake/.*
Baked Products (Science, Technology and Practice), SP Cauvain et al, Glackwell Publishing Ltd, Oxford, UK 2006, pp. 57, 59.
The Technology of Cake Making, 6th edition, EB Bennion et al, blackie Academic & Professional, Chapmann & Hall, London UK, 1997, pp. 251-288.
GRAS notification of phospholipase A2 from a genetically modified strain of *Aspergillus niger* (GRN 183), 2006.
Agency response letter GRAS notice nr. GRN 183, Jun. 2006.
Mastenbroek, "Unlimited opportuniies for new product development in the cake industry", IFT Food Expo 2007, Chicago, IL, Jul. 29, 2007.
International Search Report for PCT/EP2008/051147 mailed Jul. 14, 2008.
Database WPI Week 1988, "Sponge cake prepn.—using egg liq. Treated with phospholipase for light soft texture" & JP 63 258528, Oct. 26, 1988 (Abstract), XP002440925.
Database WPI Week 2004, "Confectionary or agent for improving quality of bread, comprising egg yolk or phospholipase treated substance of whole egg", JP 2003 325140, Nov. 18, 2003 (Abstract), XP002440926.
Database WPI Week 1987, "Cake prodn.—by adding emulsion obt. by emulsifying oil with egg yolk treated with an enzyme to cake mixt.", JP 62 111629, May 22, 1987 (Abstract). XP002440927.
Guy et al, "Application of a lipase in cake manufacture," Society of Chemical Industry, Journal of the Science of Food and Agriculture, 86, 2006, pp. 1679-1687.

(Continued)

*Primary Examiner* — D. Lawrence Tarazano
*Assistant Examiner* — Philip DuBois
(74) *Attorney, Agent, or Firm* — McBee Moore Woodward & Vanik IP, LLC

(57) ABSTRACT

The invention relates to a novel use of a phospholipase A in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. The invention also relates to a novel use of phospholipase A in the production of cake to enable reduction of the amount of eggs and/or fat used in the recipe.

25 Claims, No Drawings

(56) References Cited

OTHER PUBLICATIONS

Street, C., "Flour Confectionary manufacture," pp. 170, 174-176, Blackie: Glasgow and London, VCN Publishers, Inc., New York (1991).
Bennion, E. and Stewart, J., "Cake Manufacture and Small Goods Production," The Modern Food Industries Series, pp. 125-135, Cronshaw, H.B. (Ed.) (1930).
Littlewood, A., "Bread, Pastry and Cakes," Snack Food, pp. 36-38, Gordon Booth, R. (Ed.), An avi Book published by Van Nostrand Reinhold, New York (1990).
Japanese Office Action dated May 8, 2012 issued in Japanese Patent Application No. P2009-547687.
Marianne E. Borja, et al, 'New lower-fat dessert recipes for the school lunch program are well accepted by children', Journal of the American Dietetic Association, vol. 96, No. 9, pp. 908-910.

* cited by examiner

METHOD TO PRODUCE CAKE

This application is the U.S. national phase of International Application No. PCT/EP2008/051147 filed 30 Jan. 2008 which designated the U.S. and claims priority to European Patent Application Nos. 07101567.1 filed 1 Feb. 2007 and 07112741.9 filed 19 Jul. 2007, the entire contents of each of which are hereby incorporated by reference.

FIELD OF THE INVENTION

This invention relates to a novel method to produce cake and the cake produced with this novel method.

BACKGROUND OF THE INVENTION

Cake is known for a long time and is prepared in numerous varieties. Most cakes are made with wheat flour and therefore have some amount of gluten, which means special care needs to be taken to ensure cakes don't have a chewy texture. The cake ingredients are mixed as little as possible once the flour has been added. This differs markedly from sturdy food items made with flour such as bread, where the goal is to agitate the gluten as much as possible. The wheat flour selected to be used for cakes is often one naturally lower in gluten.

Typical cake ingredients are wheat flour, eggs and sugar. Optionally, baking powder, water, and/or fat—such as for example butter, margarine and or oil are added.

Cakes often rely on beating eggs and addition of leavening agents, such as baking powder, to produce the air bubbles in the cake. This is what makes a traditional cake fluffy and sponge-like. Therefore the type of cake ingredients and the ratio between them are important in determining cake properties such as e.g. crumb structure and cake volume.

In cake recipe's eggs are used as providers of natural emulsifiers mainly due to the presence of phospholipids that have surface-active properties. Whole eggs contain 11% lipids of which 25% is lecithin and they contain about 13% of protein.

The fat is added to entrap air during mixing, for lubrication to improve the overall eating quality in terms of moistness and tenderness, to improve the structure of the finished product, and/or to extend shelf life. Next to the beneficial effects of egg and/or fat in cake, there are some disadvantages related to the use of these ingredients.

It is known that eating of too many eggs can have detrimental effects on health, for example by increasing cholesterol.

One solution to this problem is to remove (part of) the egg in the recipe. However, in case part of the egg is removed from the recipe the cake volume some of the following effects may result: reduced, decreased batter stability, and/or deterioration of the cake texture.

The fat also has nutritional benefits but because of the high content of fat in some types of cake, such as for example the butter/margarine present in pound cake, this type of cake is a calorie booster, which can cause overweight. One solution to this problem is to remove (part of) the fat in the recipe. However, in case part of the fat is removed from the recipe the batter becomes less viscous and in some cases less stable. The baked cake has less volume, a more dense structure and mouthfeel is much drier and crumbly.

It is an object of the present invention to improve desired cake properties such as e.g. crumb structure and/or volume in regular cakes. It is another object of the present invention to enable reduction of the amount of eggs and/or fat in cake recipes, whilst at least maintaining desired cake properties, such as crumb structure and/or volume.

The objective of the present invention is reached by the use of a phospholipase A during cake production.

Therefore in a first aspect the invention relates to the use of a phospholipase A in the production of cake to enable reduction of the amount of eggs and/or fat used in the recipe.

Surprisingly, it was found that a reduction of the amount of eggs and/or fat used in the cake recipe was possible once a phospholipase A was used.

All types of phospholipase A can be used, for example phospholipase A1 or phospholipase A2. Any type of phospholipase A1 can be used. Phospholipase A1 is wide-spread in nature, e.g. in microorganisms *E. coli*, in snake venoms, and in mammals in the brain, testis and liver. An example of a suitable commercially available phospholipase A1 is Lecitase Ultra™ (Novozymes). Any type of phospholipase A2 can be used. An example of a suitable commercially available phospholipase A2 is Cakezyme™ (DSM) or Lecitase L10 (Novozymes). A preferred phospholipase A2 is porcine pancreatic phospholipase A2 for example expressed in *Aspergillus niger* (Cakezyme™, DSM).

The present invention covers all types of cake, including shortened cakes, such as for example pound cake and butter cake, and including foam cakes, such as for example meringues, sponge cake, biscuit cake, roulade, genoise and chiffon cake.

Sponge cake is a type of soft cake based on wheat flour, sugar, baking powder and eggs (and optionally baking powder). The only fat present is from the egg yolk, which is sometimes added separately from the white. It is often used as a base for other types of cakes and desserts. A basic sponge cake is made by beating the eggs with sugar until they are light and creamy, then carefully sieving and folding in the flour (which may be mixed with a small amount of baking powder, although the air incorporated into the egg mixture can be sufficient for a good rise). Sometimes, the yolks are beaten with the sugar first while the whites are beaten separately, to be mixed in later. The mixture is then poured into the chosen cake tin and baked. Before the mixture has cooled, after cooking, it is still flexible. This allows the creation of such varieties as the Swiss roll. This basic recipe is used for many treats and puddings, such as madeleines.

A pound cake is traditionally prepared of one pound each of flour, butter, eggs, and sugar, optionally complemented with baking powder.

In chiffon cake the butter/margarine has been replaced by oil. Sugar and egg yolk content has been decreased compared to pound or sponge cake and egg white content has been increased.

The reduction of the amount of eggs and/or fat which is possible according to the present invention, differs per type of cake. The man skilled in the art knows the amount of eggs and/or fat which are regularly present in cake recipes. In general a reduction of the amount of eggs of at least 5% w/w can be reached. More preferably a reduction of the amount of eggs of at least 10% w/w can be reached, even more preferably a reduction of at least 15% w/w can be reached. It was shown that even a reduction of the amount of eggs used of at least 20% w/w can be reached. The reduction of the amount of eggs can be at least 30% w/w, 40% w/w or even at least 50% w/w.

In cake recipes eggs provide natural emulsifiers as well as egg protein. Egg protein is important for froth forming in the batter and for the cake cohesiveness. In cake recipes wherein the amount of eggs has been reduced, especially if reduced of at least 30% w/w, 40% w/w or 50% w/w, the loss of egg protein can (partially) be compensated by the addition of other protein sources and/or hydrocolloids. Examples of protein sources are whey protein, soy protein, modified wheat protein, albumin, etcetera. Examples of hydrocolloids are guar gum, alginate, pectin, xanthan gum, etcetera. Therefore in one embodiment of the invention one or more protein sources and/or one or more hydrocolloids are used in the cake recipe to replace the protein content present in the eggs removed.

It has been surprisingly found that when the amount of eggs in the cake is e.g. reduced up to 50% w/w and one or more protein sources and/or one or more hydrocolloids are added to replace the egg protein, cakes can be obtained wherein desired cake properties are at least maintained.

The egg volume can (partially) be replaced by use of water. Preferably (part of) the water content of the eggs may be replaced by water. Usually an egg contains about 75% water. The amount of water used in the recipe to replace the eggs may be at least 50% of the water content of the eggs removed. More preferably at least 60% of the water content of the eggs is replaced by water, even more preferably at least 75% and most preferably 100% of the water content of the eggs removed is replaced by water. It has surprisingly been shown that the water binding properties of the cake batter and cake are improved by the use of a phospholipase A, enabling the use of more water in the cake recipe.

In general a reduction of the amount of fat of at least 10% can be reached. More preferably a reduction of the amount of fat of at least 20% can be reached, even more preferably a reduction of at least 30% can be reached. It was shown that even a reduction of the amount of fat used of at least 50% can be reached.

It was shown that it was possible when using phospholipase A to reduce the amount of eggs and/or fat used in the recipe whilst at least maintaining at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume.

In another aspect of the invention, it was found that a phospholipase A, also when retaining the same amount of eggs and/or fat used in the cake recipe, can be used in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume.

The term at least maintaining is hereby used to indicate that a property is maintained or improved.

Measuring whether a property is maintained, improved or deteriorated in general is measured by preparing a batter and/or a cake in an original recipe, not containing any phospholipase A and another batter and/or cake in a recipe containing phospholipase A and optionally less eggs and/or fat and comparing a certain property. In case the properties of both are substantially the same, the property is maintained, in case they differ either an improvement or a deterioration has taken place. For all mentioned properties below a measurement method has been given as well as an indication when a property can be considered as improved.

The batter viscosity can be measured with a Farinograph by standard methods according to the International Association of Cereal Chemistry (ICC) and the American Association of Cereal Chemistry (AACC 54-2, ICC 115).

Whether the batter viscosity has improved or deteriorated can for example be measured by comparing the batter prepared with phospholipase A, either containing or nor containing a reduced amount of eggs and/or fat, to a batter prepared without phospholipase A. In case the batter viscosity is the same for both batters, it has been maintained. In case the batter viscosity has increased, it has improved.

The specific density can be measured by weighing a predetermined volume of batter. The specific density is improved if it is decreased.

The crumb softness of the cake is evaluated either empirically by the skilled test baker or measured by the use of a texture analyzer (e.g., TAXT2) as known in the art. Actually crumb firmness is measured as is known to the person skilled in the art. The crumb softness measured within 24 hours after baking is called initial crumb softness. The crumb softness more than 24 hours after baking is called crumb softness upon storage, and is also a measure for determining shelf life. In case the initial crumb softness has increased, it has improved. In case the crumb softness upon storage has increased, it has improved.

Crumb pore homogeneity can be evaluated empirically by the skilled test baker or by digital image analysis as known in the art (e.g. C-cell, Calibre Control International Ltd, Appleton, Warrington, UK). In case the deviation in pore size is small, the crumb is called more homogeneous. In case the deviation in pore size has become smaller, the property is improved.

Crumb pore diameter can be evaluated using digital image analysis as known in the art (e.g. C-cell, Calibre Control International Ltd, Appleton, Warrington, UK). In case the average crumb pore diameter decreases, the property is improved. Preferably, this is the case when at the same time the same cake volume is maintained.

The shelf-life of the cake can be measured by determining the resilience of the cake in time. This is part of the method to measure crumb softness, as is known to the person skilled in the art, whereby the relaxation of the cake is also measured by the use of a texture analyzer (e.g., TAXT2) as known in the art.

The volume of a given cake can be determined by an automated bread volume analyser (eg. BVM-3, TexVol Instruments AB, Viken, Sweden), using ultrasound or laser detection as known in the art. In case the volume is increased, the property is improved. Alternatively the cake height after baking in the same size tin is an indication of the cake volume. In case the cake height is increased, the cake volume has increased.

The emulsion stability of the batter can be determined by determining the cake height and visual analysis of the cake structure. In case the cake height has decreased, the emulsion stability of the batter has decreased. In case the cake structure is more dense, the emulsion stability of the batter also has decreased.

In one embodiment of the invention a combination of at least two of the above-mentioned properties can be at least maintained when using phospholipase A and reducing the amount of eggs and/or fat used in the recipe or improved when using phospholipase A, such as for example: batter viscosity and specific density; batter viscosity and initial crumb softness; batter viscosity and crumb pore homogeneity; batter viscosity and crumb pore diameter; batter viscosity and crumb softness upon storage; batter viscosity and shelf life of the cake; batter viscosity and cake volume; specific density and initial crumb softness; specific density and crumb pore homogeneity; specific density and crumb pore diameter; specific density and crumb softness after storage; specific density and shelf life of the cake; specific density and cake volume; initial crumb softness and crumb pore homogeneity; initial crumb softness and crumb pore diameter; initial crumb softness and crumb softness upon storage; initial crumb softness and shelf life of the cake; initial crumb softness and cake volume; crumb pore homogeneity and crumb pore diameter; crumb pore homogeneity and crumb softness upon storage; crumb pore homogeneity and shelf life of the cake; crumb pore homogeneity and cake volume; crumb pore diameter and crumb softness upon storage; crumb pore diameter and shelf life; crumb pore diameter and cake volume; crumb softness upon storage and shelf life; crumb softness upon storage and cake volume; shelf life and cake volume.

In another embodiment of the invention a combination of at least three of the above-mentioned properties can be at least maintained when using phospholipase A and reducing the amount of eggs and/or fat used in the recipe or improved when using phospholipase A, such as for example: batter viscosity, specific density and initial crumb softness; batter viscosity, specific density and crumb pore homogeneity; batter viscosity, specific density and crumb pore diameter; batter viscosity, specific density and crumb softness after storage; batter viscosity, specific density and shelf life of the cake, batter viscosity, specific density and cake volume; specific density, initial crumb softness and crumb pore homogeneity; specific density, initial crumb softness and crumb pore homogeneity; specific density, initial crumb softness and crumb pore diameter; specific density, initial crumb softness and crumb softness upon storage; specific density, initial crumb softness and shelf life of the cake; specific density, initial crumb softness and cake volume; initial crumb softness, crumb pore homogeneity and crumb pore diameter; initial crumb softness, crumb pore homogeneity and crumb softness upon storage; initial crumb softness, crumb pore homogeneity and shelf life; initial crumb softness, crumb pore homogeneity and cake volume; crumb pore homogeneity, crumb pore diameter and crumb softness upon storage; crumb pore homogeneity, crumb pore diameter and shelf life; crumb pore homogeneity, crumb pore diameter and cake volume; crumb pore diameter, crumb softness upon storage and shelf life; crumb pore diameter, crumb softness upon storage and cake volume; crumb softness upon storage, shelf life and cake volume.

In addition also a combination of at least four of the above-mentioned properties can be at least maintained when using phospholipase A and reducing the amount of eggs and/or fat used in the recipe or improved when using phospholipase A, such as for example: batter viscosity, specific density, initial crumb softness and crumb pore homogeneity; batter viscosity, specific density, initial crumb softness and crumb pore diameter; batter viscosity, specific density, initial crumb softness and crumb softness upon storage; batter viscosity, specific density, initial crumb softness and shelf life; batter viscosity, specific density, initial crumb softness and cake volume; specific density, initial crumb softness, crumb pore homogeneity and crumb pore diameter; specific density, initial crumb softness, crumb pore homogeneity and crumb softness upon storage; specific density, initial crumb softness, crumb pore homogeneity and shelf life; specific density, initial crumb softness, crumb pore homogeneity and cake volume; initial crumb softness, crumb pore homogeneity, crumb pore diameter and crumb softness upon storage; initial crumb softness, crumb pore homogeneity, crumb pore diameter and shelf life; initial crumb softness, crumb pore homogeneity, crumb pore diameter and cake volume; crumb pore homogeneity, crumb pore diameter, crumb softness upon storage and shelf life; crumb pore homogeneity, crumb pore diameter, crumb softness upon storage and cake volume; crumb pore diameter, crumb softness upon storage, shelf life and cake volume.

In another embodiment also a combination of at least five of the above-mentioned properties can be at least maintained when using phospholipase A and reducing the amount of eggs and/or fat used in the recipe or improved when using phospholipase A, such as for example: batter viscosity, specific density, initial crumb softness, crumb pore homogeneity and crumb pore diameter; batter viscosity, specific density, initial crumb softness, crumb pore homogeneity and crumb softness upon storage; batter viscosity, specific density, initial crumb softness, crumb pore homogeneity and shelf life; batter viscosity, specific density, initial crumb softness, crumb pore homogeneity and cake volume; specific density, initial crumb softness, crumb pore homogeneity, crumb pore diameter and crumb softness upon storage; specific density, initial crumb softness, crumb pore homogeneity, crumb pore diameter and shelf life; specific density, initial crumb softness, crumb pore homogeneity, crumb pore diameter and cake volume; initial crumb softness, crumb pore homogeneity, crumb pore diameter, crumb softness upon storage and shelf life; initial crumb softness, crumb pore homogeneity, crumb pore diameter, crumb softness upon storage and cake volume; crumb pore homogeneity, crumb pore diameter, crumb softness upon storage, shelf life and cake volume.

In yet another embodiment also a combination of at least six of the above-mentioned properties can be at least maintained when using phospholipase A and reducing the amount of eggs and/or fat used in the recipe or improved when using phospholipase A, such as for example: batter viscosity, specific density, initial crumb softness, crumb pore homogeneity, crumb pore diameter and crumb softness upon storage; batter viscosity, specific density, initial crumb softness, crumb pore homogeneity, crumb pore diameter and shelf life; batter viscosity, specific density, initial crumb softness, crumb pore homogeneity, crumb pore diameter and cake volume; specific density, initial crumb softness, crumb pore homogeneity, crumb pore diameter, crumb softness upon storage and shelf life; specific density, initial crumb softness, crumb pore homogeneity, crumb pore diameter, crumb softness upon storage and cake volume; initial crumb softness, crumb pore homogeneity, crumb pore diameter, crumb softness upon storage, shelf life and cake volume.

In a preferred embodiment all indicated properties are at least maintained when using phospholipase A and reducing the amount of eggs and/or fat used in the recipe or improved when using phospholipase A.

In a third aspect the invention relates to a method to prepare a cake comprising the steps of:
  a. preparing the batter of the cake by adding at least:
    i. sugar
    ii. flour
    iii. (a) phospholipase A and egg or
      (b) egg pre-treated with phospholipase A, optionally obtained by adding a phospholipase A to an egg in an amount sufficient to yield a conversion of between 10 to 70% of the lecithin present in the egg to lysolecithin.
  b. putting the batter in a suitable baking mould
  c. baking the cake.

According to the above-mentioned method both cakes comprising a reduced amount of eggs and/or fat and cakes where no eggs and/or fat reduction has been applied can be prepared.

In another aspect the invention relates to a method to prepare a batter of a cake comprising adding at least
i. sugar
ii. flour
iii. (a) phospholipase A and egg or
   (b) egg pre-treated with phospholipase A, optionally obtained by adding a phospholipase A to an egg in an amount sufficient to yield a conversion of between 10 to 70% of the lecithin present in the egg to lysolecithin.

There are several methods to combine cake ingredients, for example:
  Creaming method—butter and sugar are creamed together before the rest of the ingredients are gradually added.
  Melt-and-mix—dry ingredients are mixed together and then melted butter and other liquids are added to complete the cake.
  'All-in-together'—the dry ingredients and shortening are placed in the food processor and liquid is gradually added.
  Sponge cake production—eggs and sugar are whipped to a froth and flour is carefully mixed in. No fat is used in this method.

When all the cake ingredients are mixed, the mixture is called cake batter.

The phospholipase A can be added during various stages of the cake production.

In one embodiment of the invention, the phospholipase A can be used to pre-incubate the egg. The egg can be pre-incubated whole, alternatively only the yolk or only the egg-white can be incubated. It has been found that it is advantageous to retain some lecithin in the egg for some applications. Therefore, in a preferred embodiment, the time the egg is incubated with the phospholipase A is limited to still retain some lecithin. Preferably between 10-70% of the lecithin present in the used eggs should be hydrolysed into lysolecithin. More preferably at least 20% lecithin should be hydrolysed and even more preferably at least 30%. In another preferred embodiment at most 60% lecithin should be hydrolysed and even more preferably at most 50% lecithin should be hydrolysed. Alternatively, incubated egg containing almost no remaining lecithin can be mixed with some non-incubated egg or some lecithin to obtain the desired quantities of lecithin and lysolecithin. The pre-incubated egg, or egg-mixture can be added to the other cake ingredients in liquid or in dried powder form. Methods to prepare a powder of eggs are known in the art. Powder form egg is also suitable for use in cake mixes not needing any eggs added thereto.

In an alternative embodiment, the phospholipase A is added during preparation of the batter and is allowed to act in-situ. This embodiment has as advantage that pre-incubation of the egg is not needed, thereby reducing the time needed to prepare the cake. Also in this case it is preferred to retain some lecithin in the cake mixture, analogous to the preferences given above.

In a preferred embodiment, which can be applied to all aspects of the invention, additionally at least one of the compounds selected from the group consisting of calcium, yeast extract, modified starch, lipase and/or amyloglucosidase is combined with the phospholipase A in the production of the cake. The cake can either be a regular cake, i.e. a cake comprising a regular amount of eggs and/or fat or a cake where eggs and/or fat have been reduced. The man skilled in the art knows which amount of eggs and/or fat is present in regular cakes, which amount will be dependent on the type of cake.

In a preferred embodiment of any one of the aspects of the invention also calcium is added to enhance the activity of the phospholipase A either at the pre-incubation or during the preparation of the batter to enhance the in-situ action of the phospholipase. In a preferred embodiment the calcium is added during preparation of the batter. It has been found especially advantageous to add approximately between 40-200 mg $CaCl_2.H_2O$ per 5,000 CPU Phospholipase A (hereafter indicated as PLA) to the cake recipe. Preferably, between 50 and 150 mg $CaCl_2.H_2O$ per 5,000 CPU PLA is added to the cake recipe and most preferably at least 90 mg $CaCl_2.H_2O$ per 5,000 CPU PLA. CPU (Chromogenic Phospholipase Unit=1 EYU (Egg Yolk Unit) is defined as the amount of enzyme that liberates 1 μmol of acid per minute from egg yolk at 40° C. and pH8.0. Substrate in this method: rac 1,2-dioctanoyldithio phosphatidylcholine measured spectrophotometric at 405 nm. Surprisingly, has been found that the cake batter does not provide enough calcium for the phospholipase A to work efficiently.

Typical ingredients of the cake are wheat flour, eggs and sugar. Optionally, baking powder, salt, water, emulsifiers (such as for example PGE's and monoglycerides), margarine, butter and/or oil are added (for example for pound cakes and muffins).

Also components to improve waterbinding such as hydrocolloids or modified starch can be used. In one embodiment of the invention, which can be applied to all the aspects of the invention, modified starch can be used to reduce the amount of fat used in the recipe even further. All types of modified starch can be used, for example modified potato starch or modified wheat starch. Preferably modified potato starch is used, such as for example disclosed in U.S. Pat. No. 6,864,063. Most preferably modified potato starch is used which is obtained by treating potato starch with amylomaltase, more preferably with amylomaltase derived from *Bacillus amyloliquefaciens*. An example of modified potato starch obtained by treating potato starch with amylomaltase derived from *Bacillus amyloliquefaciens* is sold under the trademark Etenia® (Avebe Food). It has been surprisingly found that in cakes comprising a reduced amount of fat, e.g. as low as 30% w/w, and which are prepared using a combination of phospholipase A and modified potato starch, desired cake properties as those mentioned above, e.g. batter viscosity, are improved if compared with cakes produced by using 30% w/w less fat and no addition of phospholipase A and modified potato starch.

Optionally, flavouring agents such as vanilla extract, cocoa powder or yeast extracts can be added. An example of a suitable yeast extract is a yeast extract comprising at least 30% w/w 5' ribonucleotides on the basis of sodium free dry matter.

In a preferred embodiment of the invention, which can be applied to all the aspects of the invention, a yeast extract is used which comprises at least 30% w/w 5'-ribonucleotides, preferably at least 34% w/w, 38% w/w, 40% w/w or 42% w/w, more preferably at least 44% w/w, 46% w/w, 48% w/w or at least 50% w/w 5'-ribonucleotides on the basis of sodium chloride free dry matter. It has been found that the use of such yeast extract not only improves the taste of the cake, but also has a surprising emulsifying effect, since upon its use, the viscosity of the batter improves.

In the context of the present invention, the phrase "5'-ribonucleotides" refers to the total amount of 5'-monophosphate ribonucleotides formed during RNA degradation, viz. 5'-monophosphate guanine (5'-GMP), 5'-monophosphate uracil (5'-UMP), 5'-monophosphate cytosine (5'-CMP), 5'-monophosphate adenine (5'-AMP), where 5'-AMP may be partially or completely converted into 5'-monophosphate inosine (5'-IMP). For example, in a yeast extract which comprises 30% w/w 5'-ribonucleotides on the basis of sodium chloride free dry matter, the total amount of 5'-GMP, 5'-UMP, 5'-CMP, 5'-AMP and 5'-IMP is 30% w/w on the basis of sodium chloride free dry matter.

In a preferred embodiment, a yeast extract is used wherein the total amount of 5'-GMP plus 5'-IMP is at least 15% w/w, preferably at least 17% w/w, 19% w/w, 20% w/w or 21% w/w, more preferably at least 22% w/w, 23% w/w, 24% w/w or 25% w/w, on the basis of sodium chloride free dry matter. Due to the constitution of RNA, from which the 5'-ribonucleotides arise, 5'-GMP and 5'-IMP will always be present in approximately equal amounts in this embodiment.

In the context of the present invention, weight percentage calculations of the 5'-ribonucleotides are based on the disodium salt heptahydrate thereof unless otherwise specified. All percentages are calculated on sodium chloride free dry matter. In the present invention, the phrase 'sodium chloride free dry matter' refers to the fact that for the calculation of the weight percentage the weight of any sodium chloride present is excluded from the composition. The measurement of sodium chloride in the composition and the above-mentioned calculation can be performed by methods known to those skilled in the art. An example of yeast extracts comprising 40% w/w 5'-ribonucleotides of which 20% w/w 5'-GMP plus 5'-IMP, weight percentages being based on sodium chloride free yeast extract dry matter, is sold under the trademark Maxarite® Delite (DSM Food Specialties, The Netherlands).

The yeast extract may be prepared by any method which yields a yeast extract which comprises at least 30% w/w 5'-ribonucleotides on the basis of sodium chloride free dry matter.

The yeast extract may be obtained by hydrolysis or autolysis. Methods to produce hydrolytic yeast extracts are known in the art, see for example WO88/05267. In another embodiment, the yeast extract is obtained by autolysis, for instance as described in WO2005/067734.

It is possible to add additional enzymes to the cake ingredients. Examples of such enzymes are amylolytic enzymes like fungal alpha-amylase, bacterial amylases, anti-staling amylases, amyloglucosidases, lipolytic enzymes like lipases, galactolipases, proteolytic enzymes like endoproteases and exoproteases (carboxy- and aminopeptidases, redox enzymes (oxidases, etc.) and cross-linking enzymes (transglutaminase, etc).

In a preferred embodiment amyloglucosidase is added during the cake production process. Amyloglucosidase has been found to have a positive effect on the batter viscosity and resulting in a finer crumb structure. Furthermore, the amyloglucosidase has a sweetening effect on the taste of the cake.

In another preferred embodiment, which can be applied to all aspects of the invention, another lipolytic enzyme, for example a lipase is added during the cake production process in combination with Phospholipase A. Surprisingly, it was found that adding an additional lipolytic enzyme increases the emulsion stability of the batter. Examples of suitable lipolytic enzymes are Bakezyme® L80,000 (a *R. oryzae* lipase, available from DSM Food Specialties, The Netherlands) or Lipopan® 50 (a *T. lanuginosis* lipase, available from Novozymes, Denmark). An additional advantage is that this enables reduction of chemical emulsifier components, such as mono- and or diglycerides (E471) and polyglycerol esters of fatty acids (E475). The lipase can be added in a dosage between 0.5-5 wt % per kg of flour. In another aspect, the invention therefore relates to the use of a lipase in cake production for stabilizing the batter emulsion.

In one embodiment of the invention, which can be applied to all aspects of the invention, the phospholipase A and the optional additional ingredients are present in a cake mix. Cake mixes are often used at home because they are convenient. Most cake mixes simply require adding the package contents to eggs and oil in a bowl and mixing for two to three minutes. The mixture is then ready to be poured into pans and baked.

In a preferred embodiment of the invention, which can be applied to all aspects of the invention, additionally at least one of the compounds selected from the group consisting of calcium, yeast extract, modified starch, lipase and/or amyloglucosidase is used or added to the batter in combination with Phospholipase A. Also a combination of these compounds is possible, for example the addition of both calcium and yeast extract, the addition of both yeast extract and modified starch, the addition of both lipase and yeast extract, the addition of both amyloglucosidase and lipase, the addition of both lipase and modified starch, the addition of both modified starch and amyloglucosidase. In a preferred embodiment of the invention, which can be applied to all aspects of the invention, both yeast extract, according to the preferences indicated above, and modified starch according to the preferences indicated above is used or added to the batter or cake mix in combination with phospholipase A. The yeast extract preferably comprises 30% w/w 5'-ribonucleotides on the basis of sodium chloride free yeast extract dry matter, preferably wherein the total amount of 5'-GMP plus 5'-IMP in the yeast extract is at least 15% w/w, preferably at least 17% w/w, 19% w/w, 20% w/w or 21% w/w, more preferably at least 22% w/w, 23% w/w, 24% w/w or 25% w/w, on the basis of sodium chloride free yeast extract dry matter. The modified starch is modified starch is preferably modified potato starch, preferably a modified potato starch obtained by treating potato starch with amylomaltase derived from *Bacillus amyloliquefaciens* It has been surprisingly found that cake containing 30% less butter, 20% less eggs, and a combination of phospholipase A, modified potato starch and a yeast extract comprising at least 30% w/w 5'-ribonucleotides on the basis of sodium chloride free dry matter, has very good quality in terms of volume, structure, mouthfeel and taste. This cake is very similar to the reference but containing much less calories per unit of weight.

The invention is hereby illustrated with the following non-limiting examples

Example 1

Effect of Phospholipase on Pound Cake Batter Viscosity

Pound cake batters were prepared from 750 g Damco™ cake mix, 375 g whole liquid egg, 375 g butter, 4.5 g salt and various quantities of phospholipase. As phospholipase Cakezyme™ (DSM Food Specialties, The Netherlands) was used, a phospholipase A2 produced by *A. niger* containing 5000 CPU/g indicated as PLA in the tables. CPU (Chromogenic Phospholipase Unit=1 EYU (Egg Yolk Unit) is defined as the amount of enzyme that liberates 1 μmol of acid per minute from egg yolk at 40° C. and pH8.0. Substrate in this method: rac 1,2-dioctanoyldithio phosphatidylcholine measured spectrophotometric at 405 nm. The quantity of enzyme applied is expressed as a percentage of the mass of the whole liquid egg present in the reference recipe.

All ingredients are brought into a Hobart mixer provided with a flat beater mixer and mixed for 1 minute in speed 1 and 3 minutes in speed 2.

Afterward batter viscosity was analyzed with use of a Brookfield rheometer provided with a spindle no. 7 at 30 rpm. Results are shown in Table 1.

TABLE 1

Effect of phospholipase on viscosity of batter in different compositions

| | Cakemix + salt (g) | Butter (g) | Egg (g) | Water (g) | Modified starch* (g) | Cakezyme ™ (g) | Viscosity (mPa) |
|---|---|---|---|---|---|---|---|
| Reference | 750 + 4 | 375 | 375 | — | — | — | 61200 |
| +0.1% PLA | 750 + 4 | 375 | 375 | — | — | 0.375 | 67736 |
| +0.2% PLA | 750 + 4 | 375 | 375 | — | — | 0.750 | 71321 |
| Ref. - 30% butter | 750 + 4 | 263 | 375 | 90** | — | — | 16667 |
| +0.1% PLA | 750 + 4 | 263 | 375 | 90 | 12 | 0.375 | 25600 |
| +0.2% PLA | 750 + 4 | 263 | 375 | 90 | 12 | 0.750 | 34267 |
| Ref. - 30% butter - 20% egg | 750 + 4 | 263 | 300 | 146*** | — | — | 21067 |
| +0.1% PLA | 750 + 4 | 263 | 300 | 146 | 12 | 0.375 | 45600 |
| +0.2% PLA | 750 + 4 | 263 | 300 | 146 | 12 | 0.750 | 43467 |

*Etenia (Avebe Food) is enzyme-modified starch added to the recipe to bind extra added water.
**Butter consists for 80% of water. Water content of reduced quantity of fat is added to the recipe.
***Egg consists for 75% of water. Water content of reduced quantity of eggs is also added to the recipe.

From these results it is clear that addition of the phospholipase A results in an increase of viscosity.

From the results it is also clear that a batter produced with 30% less butter, has a seriously decreased batter viscosity. The viscosity is improved by introduction of phospholipase A, and modified starch.

When besides part of the butter also part of the egg are left out a somewhat higher viscosity is found compared to that of the batter produced with only 30% reduction of butter. Introduction of phospholipase and modified starch also here results in a relative strong increase of batter viscosity.

Example 2

The Effect of Phospholipase on Sponge Cake Volume, Specific Density, Crumb Softness and Shelf Life For sponge cake production batters were prepared from 250 g GB Kapsel-biscuit mix (Dethmers), 200 g whole liquid egg, 25 g water and various quantities of Cakezyme™. The ingredients were mixed into a batter using a Hobart mixer provided with a wire whisk mixer for 1 minute at speed 1, 7 minutes at speed 3 and 1 minute at speed 1.

Specific density of the batter was measured by filling a 300 ml cup with batter and weighing the cup afterwards.

400 g batter was put in a baking pan (diameter 25 cm) and baked for 25 minutes at 170° C.

Height of cakes was determined by averaging the heights measured at the two sides and in the middle of the sponge cake.

Softness of the crumb was determined by averaging the firmness values obtained by use of a Texture analyzer at two sides and the middle of the cake. Also the resilience of the crumb was determined. Firmness and resilience were analyzed after storing the sponge cakes for 4 days at room temperature. The sponge cakes were stored separately in polythene bags.

Results are shown in Table 2.

TABLE 2

The effect of phospholipase on sponge cake height

| Cakezyme ™ (% calculated on egg mass) | Specific density (g/ltr) | Average cake height (mm) | Crumb firmness after 4 days (A.U) | Resilience after 4 days (%) |
|---|---|---|---|---|
| — | 320 | 42 | 157 | 58.4 |
| 0.025 | 319 | 43 | 132 | 59.8 |
| 0.05 | 317 | 45 | 110 | 58.6 |
| 0.1 | 314 | 47 | 98 | 59.7 |

From these results it is clear that phospholipase action on egg lipids results in decrease of the specific density and increase of volume expressed as increase in height of the baked cake.

The crumb structure of the sponge is also improved. The reference showed a regular, somewhat open structure while the cakes containing 0.025 and 0.05% Cakezyme™ had a finer and even more regular structure. Cake containing the highest level of phospholipase showed a more open structure and was a little bit crumbly.

Softness of the crumb after 4 days of shelf life showed to be better for the sponge cakes produced with phospholipase compared to the softness of the reference. Crumb resilience was similar in all cases.

Storage of sponge cakes in the freezer over a period of 8 weeks did not change the relative differences in crumb softness and resilience.

Example 3

The Effect of Phospholipase on Sponge Cake Volume, Specific Density and Consistency at Reduced Egg Content For sponge cake production batters were prepared from 1250 g GB Kapsel-biscuit mix (Dethmers), 125 g water, 0.04% Cakezyme™ (calculated on total egg weight present in reference recipe) and various levels of whole liquid egg.

To compensate for the loss of water (eggs contain 75% water) 50 to 100% of this loss was extra added The ingredients were mixed into a batter using a (large) Hobart mixer provided with a wire whisk mixer for 1 minute at speed 2, 6 minutes at speed 3 and 1 minute at speed 1.

Specific density of the batter was measured by filling a 300 ml cup with batter and weighing the cup afterwards.

2000 g batter was spread on a baking plate (40×60 cm) and baked for 30 minutes at 180° C.

Height of cakes was determined by averaging the heights measured at the two sides and in the middle of the sponge cake.

Results are shown in Table 3.

TABLE 3

The effect of phospholipase on sponge cake height at reduced egg content

| Sponge cake mix (g) | Eggs (g) | Water (ml) | Cakezyme (% on total eggs) | Density (g/ltr) | Cake height (mm) | Consistency |
|---|---|---|---|---|---|---|
| 1250 | 1000 (100%) | 125 | — | 320 | 62 | Good |
| 1250 | 800 (80%) | 125 | — | 330 | 54 | Less coherent |
| 1250 | 800 (80%) | 125 | 0.04 | 320 | 60 | Good |
| 1250 | 800 (80%) | 200 (+50% egg water) | 0.04 | 313 | 62 | Good |

From these results it is clear that the egg content in the recipe may be reduced by 20% when 0.04% Cakezyme™ and 50% of the water present in the 20% eggs left out of the recipe. The organoleptic characteristics of the alternative are similar to those of the reference.

Example 4

The Effect of Phospholipase on Pound Cake Volume, Texture and Crumb Softness

Pound cakes were prepared from 375 g whole liquid eggs, 375 g sugar (Castor extra), 375 g cake margarine, 375 g flour (Albatros, Meneba), 37.5 g BV 40 (DMV) emulsifier, 4.5 g SAPP 15, 3 g sodium bicarbonate and various levels of Cakezyme™ The margarine was melted by mixing in a Hobart provided with a flat beater mixer during 1 minute at speed 1 and 1 minute at speed 3. Afterwards the other ingredients were added and mixed for 1 minute at speed 1 and 5 minutes at speed 2. Five cake pans were filled with 300 g batter and baked for 60 minutes at 160° C.

Cake height was measured in the middle of cake. Cake height of reference was defined as 100%. Crumb firmness was measured on 2 slices cut in the middle of cake having a thickness of 2.0 cm with use of a texture analyzer. No preservatives added to the recipes all cakes were still clean from microbial contamination after 8 weeks of storage at room temperature.

Results are shown in Table 4.

TABLE 4

The effect of phospholipase on pound cake height, texture, crumb firmness and shelf life

|  | Reference | Reference + 0.1% Cakezyme ™ |
|---|---|---|
| Batter quality | Good | Thicker |
| Volume | 100% | 105% |
| Crumb structure | Regular, fine | Regular, finer |
| Crumb firmness initially | 100% | 80% |
| after 4 wks | 103% | 93% |
| after 8 wks | 141% | 109% |

From these results it is clear that phospholipase has a distinct influence on volume of the cake, on the crumb structure and on firmness both initially and during shelf life.

Example 5

Effect of Phospholipase on Pound Cake Quality at 20% Egg Reduction

Pound cake was produced according to the method and the recipe described in Example 4 with the exception that in this example egg content is varied. The egg content was reduced by 20%. The total reduction in recipe mass is 75 g of which 56 g is water (egg contains around 75% water). This quantity of water was added in one trial.

In Table 5 the results are shown for batter quality, cake height (measured in the middle of the cake), structure and firmness over a storage period of 8 weeks. Both volume and initial firmness value of the reference is set at 100%. All other firmness values are calculated as a percentage of the value.

TABLE 5

Effect of phospholipase on pound cake quality at 20% egg reduction

| Eggs (g) | Water (ml) | Cakezyme ™ (% on total eggs) | Batter quality | Cake height (%) | Structure | Firmness (0 → 8 wks) |
|---|---|---|---|---|---|---|
| 375 | 0 | 0 | Good | 100 | Regular, open | 100% → 141% |
| 300 (80%) | 0 | 0 | Less* viscous | 91 | Coarse | n.d. |
| 300 (80%) | 0 | 0.1 | More* viscous | 95 | Coarse, bright | 95% → 128% |
| 300 (80%) | 56 | 0.1 | ~equal* | 105 | Fine, bright | 88% → 118% |

*compared to reference viscosity
n.d = not determined

From these results it is clear that reduction of egg content by 20% can be compensated by the addition of 0.1% Cakezyme™ and the quantity of water present in left out eggs. In this case even the cake height increased by 5% and the crumb structure was finer and brighter than seen in the reference cake.

Example 6

Effect of Phospholipase on Pound Cake Quality at 20% Fat Reduction

Pound cakes were produced according to the method and the recipe described in Example 4 with the exception that in this example fat content is varied. The fat content was reduced by 20%. The total reduction in recipe mass is 75 g of which 60 g is water. In initial trials this quantity of water was added but 100% mass replacement with water gave better results. Fat contributes to taste and mouthful. Reduction of fat in the recipe leads to less taste in the baked product. For this reason in one of the trials Maxarite™ Delite (DSM Food Specialties, The Netherlands) was added being a yeast-derived taste enhancer. Maxarite™ Delite comprises 40% w/w 5'-ribonucleotides of which 20% w/w 5'-GMP plus 5'-IMP and less than 0.1% w/w NaCl based on yeast extract dry matter.

Crumb firmness was determined with use of a texture analyzer. Taste and mouthfeel was analyzed by a non-trained consumer panel.

Results are shown in Table 6.

From these results conclusions are that reduction of fat results in a drier, less cohesive type of cake. Addition of phospholipase A (Cakezyme™, DSM) restores part of these negative effects and also increases cake height by 14%. Combination of phospholipase and Maxarite™ gave an overall cake quality similar to the reference in terms of cohesiveness, taste and mouthfeel. This combination increased cake height by 12%.

Example 7

Effect of Phospholipase on Pound Cake Quality at 30% Fat Reduction in Combination with 20% Egg Reduction Pound cake batters were prepared from 750 g Damco™ cake mix, 375 g or 300 g whole liquid egg, 375 g or 263 g butter, 4.5 g salt and various quantities of phospholipase. Batters were mixed as described in Example 1. Viscosities were determined as described in Example 1.

4×425 g batter was weighed in cake pans and baked for 60 minutes at 160° C.

Cake height was determined in the middle of the cake.
Taste was analyzed by a non-trained consumer panel.

TABLE 6

Effect of phospholipase on pound cake quality at 20% fat reduction

| Butter (g) | Water (g) | Cakezyme ™ (% on total eggs) | Maxarite ™ (% on total weight) | Batter quality | Cake height (%) | Structure | Firmness (0 → 8 wks) | Taste and mouth-feel |
|---|---|---|---|---|---|---|---|---|
| 375 | 0 | 0 | 0 | Good | 100 | Regular, open | 100% → 141% | Cake |
| 300 (80%) | 75 | 0 | 0 | Much* less viscous | 102 | Fine | n.d | Loose, dry |
| 300 (80%) | 75 | 0.1 | 0 | Less* viscous | 114 | Fine | 76% → 131% | Cake, dry |
| 300 (80%) | 75 | 0.1 | 0.1 | Less* viscous | 112 | dense | n.d | Cake |

*compared to reference viscosity.
n.d = not determined

Results are shown in Table 7.

TABLE 7

Effect of phospholipase on pound cake quality at 30% fat reduction in combination with 20% egg reduction

| Butter (g) | Eggs (g) | Water (ml) | Cakezyme ™ (% on total eggs) | Modified starch (% on total weight) | Maxarite ™ (% on total weight) | Batter viscosity (mPa) | Cake height (%) | Structure | Mouth feel |
|---|---|---|---|---|---|---|---|---|---|
| 375 | 375 | 0 | 0 | 0 | 0 | 61200 | 100 | Regular, open | Good |
| 263 (70%) | 375 | 90 | 0 | 0 | 0 | 16667 | 89 | Fine → dense | dry |
| 263 (70%) | 375 | 90 | 0.2 | 0 | 0 | 24937 | 98 | Fine | Less dry |
| 263 (70%) | 375 | 90 | 0.2 | 0.8 | 0 | 34267 | 95 | Dense | Less dry |
| 263 (70%) | 375 | 146 | 0.2 | 0.8 | 0 | 32800 | 99 | Regular, fine | Good |
| 263 (70%) | 300 (80%) | 146 | 0 | 0 | 0 | 21067 | 87 | Open | Dry, less cohesive |
| 263 (70%) | 300 (80%) | 146 | 0.2 | 0.8 | 0 | 43467 | 92 | Regular, fine | Cohesive, less buttery |
| 263 (70%) | 300 (80%) | 146 | 0.2 | 0.8 | 0.1 | 43133 | 96 | Regular, fine | Like reference |

Reduction of fat and eggs lowers batter's viscosity severely. Introduction of phospholipase restores viscosity partly. When Etenia™ is added viscosity is further restored, but not to the level of the reference viscosity.

After baking the result for the cake containing 30% less butter, 0.2% Cakezyme™, 0.8% Etenia™, and 146 ml water has good quality but less taste compared to reference.

The result for the cake containing 30% less butter, 20% less eggs, 0.2% Cakezyme™, 0.8% Etenia™, 0.1% Maxarite™ and 146 ml water has very good quality in terms of volume, structure, mouthfeel and taste. This cake is very similar to the reference but containing much less calories per unit of weight.

Example 8

Effect of Lipase and Phospholipase on Pound Cake Quality at 50% Emulsifier Reduction Pound cake batters were prepared from 500 g cake flour (Albatros, Meneba), 500 g Castor sugar, 500 g Cake margarine, 500 g whole liquid eggs, 60 g BV 40 (DMV), 7 g salt, 4 g sodium bicarbonate and 6 g BP Pyro Sapp 22. Batters were mixed as described in Example 1. 4×425 g batter was weighed in cake pans and baked for 60 minutes at 160° C. Cake height was determined in the middle of the cake. Cake structure was determined visually. Taste was analyzed by a non-trained consumer panel. The results are shown in Table 8.

TABLE 8

Effect of lipase and phospholipase on pound cake quality at 50% emulsifier reduction

| BV 40 (g) | Cakezyme ™ (% on total eggs) | Bakezyme L80.000B (ppm) | Cake height (%) | Structure | Mouthfeel |
|---|---|---|---|---|---|
| 60 | 0 | 0 | 100 | Regular, open | Good |
| 30 | 0 | 0 | 76 | Dense, Starch layer | Wet, starchy |
| 30 | 0 | 30 | 92 | Fine, Small starch layer | Cohesive, little bit starchy |
| 30 | 0 | 60 | 101 | Regular, fine | Good, cohesive |
| 30 | 0.1 | 60 | 106 | Regular, fine | Good, cohesive, buttery |

Reduction of BV 40 as stabilizer lowers the emulsion stabilization of the batter drastically. After baking the cake containing 50% less stabilizer collapses, resulting in a lower cake height. The structure is dense and shows a layer of starchy material. Addition of 30 ppm lipase Bakezyme L80.000B shows to be able to improve the emulsion stabilization of the batter to a certain extent. Introducing 60 ppm lipase Bakezyme L80.000B does restore the emulsion stability, the volume is similar to the reference, and the crumb structure is regular and fine. This cake shows to have a good taste. Combination of lipase and phospholipase even further improves the quality in terms of volume and organoleptic characteristics.

The invention claimed is:

1. A method of preparing a batter of a cake having a reduced amount of egg relative to an original recipe and optionally a reduced amount of fat relative to an original recipe, the method comprising:
    providing an original recipe;
    modifying the original recipe by combining
    (a) sugar in an amount called for in the original recipe; and
    (b) flour in an amount called for in the original recipe; and (c) either: (c1) phospholipase A and egg, or (c2) egg pretreated with phospholipase A; and
(d) optionally, a fat; and
reducing the amount of egg by at least 5% w/w relative to the amount of egg called for in the original recipe; and optionally reducing the amount of fat by at least 10% w/w relative to the amount of fat called for in the original recipe, wherein the amount of phospholipase A added is sufficient to increase viscosity of the batter or to decrease specific density of the batter relative to the batter having the reduced amount of egg relative to the original recipe and optionally the reduced amount of fat relative to the original recipe made without phospholipase A, and wherein the original recipe is a recipe for a batter of a cake which does not contain phospholipase A selected from the group consisting of a pound cake, a butter cake, a sponge cake, a genoise, a muffin, and a chiffon cake.

2. The method of claim 1, wherein said batter additionally contains at least one protein source or hydrocolloid to replace the protein content present in the reduced amount of eggs.

3. The method of claim 1, wherein said batter contains a reduced amount of eggs, said batter further comprising an amount of water to replace the water content present in the reduced amount of eggs.

4. The method of claim 1, wherein said batter additionally comprises at least one of calcium, yeast extract, modified starch, lipase or amyloglucosidase.

5. The method of claim 4, wherein phospholipase A is combined with calcium.

6. The method of claim 4, wherein the phospholipase A is combined with at least one of a yeast extract or a modified starch.

7. The method of claim 6, wherein the yeast extract comprises 30% w/w 5'-ribonucleotides on the basis of sodium chloride free yeast extract dry matter.

8. The method of claim 4, wherein the batter additionally comprises a lipase.

9. The method of claim 1, wherein said batter further comprises at least one enzyme selected from the group consisting of an amylolytic enzyme, a lipolytic enzyme, a proteolytic enzyme, and a cross linking enzyme.

10. The method of claim 3, wherein the amount of water additionally contained is at least 50% w/w of the water content of the eggs.

11. The method of claim 5, wherein calcium is present in an amount of 40-200 mg $CaCl_2 \cdot H_2O$ per 5,000 CPU Phospholipase A.

12. The method of claim 7, wherein the total amount of 5'-GMP plus 5'-IMP in the yeast extract is at least 15% w/w, on the basis of sodium chloride free yeast extract dry matter.

13. The method of claim 12, wherein the total amount of 5'-GMP plus 5'-IMP in the yeast extract is at least 24% w/w.

14. The method of claim 1, wherein the egg is pre-treated with phospholipase A by adding a phospholipase A to the egg in an amount sufficient to yield a conversion of 10 to 70% of lecithin present in the egg to lysolecithin.

15. The method of claim 1, wherein the amount of egg in the batter is reduced by at least 20% w/w relative to the original recipe.

16. The method of claim 1, wherein the amount of fat in the batter is reduced by at least 20% w/w relative to the original recipe.

17. The method of claim 1, wherein the amount of fat in the batter is reduced by at least 30% w/w relative to the original recipe.

18. The method of claim 1, wherein the batter has a maintained or increased viscosity and a maintained or decreased specific density relative to a batter made according to the original recipe.

19. The method of claim 1, wherein a cake made from the batter has at least one property relative to a cake made from a batter made without phospholipase A selected from the group consisting of: increased initial crumb softness, increased crumb pore homogeneity, decreased crumb pore diameter, increased crumb softness upon storage, increased shelf life, and increased cake volume of a cake made with the batter.

20. The method of claim 1, wherein a cake made from the batter has at least one property relative to a cake made from the original recipe selected from the group consisting of: maintained or increased initial crumb softness, maintained or increased crumb pore homogeneity, maintained or decreased crumb pore diameter, maintained or increased crumb softness upon storage, maintained or increased shelf life, and maintained or increased cake volume of a cake made with the batter.

21. The method of claim 1, wherein the batter comprises egg yolk.

22. The method of claim 1, wherein the egg provides a phospholipid having a surface-active property.

23. The method of claim 1, wherein the cake batter does not comprise an anti-staling amylase.

24. A method of making a cake having a reduced amount of at least one of egg and fat relative to an original recipe, the method comprising:
(a) providing an original recipe for a batter; and
modifying the original recipe for the batter by combining:
(1) sugar in an amount called for in the original recipe; and
(2) flour in an amount called for in the original recipe; and
(3) either: (3i) phospholipase A and egg, or (3ii) egg pretreated with phospholipase A; and
(4) optionally, a fat; and
reducing the amount of egg by at least 5% w/w relative to the amount of egg called for in the original recipe; and optionally reducing the amount of fat optionally is reduce by at least 10% w/w relative to the amount of fat called for in the original recipe, wherein the amount of phospholipase A added is sufficient to increase viscosity of the batter or to decrease specific density of the batter relative to the batter having the reduced amount of at least one of egg and fat made without phospholipase A, and wherein the original recipe is a recipe for a batter of a cake which does not contain phospholipase A selected from the group consisting of a pound cake, a butter cake, a sponge cake, a genoise, a muffin, and a chiffon cake; and
(b) baking the batter in a suitable baking mold to obtain the cake;
wherein at least one property selected from the group consisting of initial crumb softness, crumb pore homogeneity, crumb pore diameter, crumb softness upon storage, shelf life and cake volume, is maintained or increased in the cake relative to a reference cake made from a batter according to the original recipe, but which does not comprise phospholipase A.

25. A method of preparing a batter of a shortened cake or a foam cake having a reduced amount of fat relative to an original recipe, and optionally a reduced amount of egg relative to an original recipe, the method comprising providing an original recipe; and modifying the original recipe by combining at least:

(a) sugar in an amount called for in the original recipe; and (b) flour in an amount called for in the original recipe; and (c) either: (c1) phospholipase A and egg, or (c2) egg pretreated with phospholipase A; and (d) a fat; and reducing the amount of fat by at least 10% w/w relative to the amount of fat called for in the original recipe; or reducing the amount of fat by at least 10% w/w relative to the amount of fat called for in the original recipe and reducing the amount of egg by at least 5% w/w relative to the amount of egg called for in the original recipe, wherein the amount of phospholipase A added is sufficient to increase viscosity of the batter or to decrease specific density of the batter relative to the batter having the reduced amount of fat relative to the original recipe, and optionally the reduced amount of egg relative to the original recipe made without phospholipase A, wherein said shortened cake is selected from the group consisting of pound cake, butter cake, and muffin, and wherein said foam cake is selected from the group consisting of roulade, genoise, and chiffon cake.

* * * * *